United States Patent [19]

Pedain et al.

[11] Patent Number: 5,068,402
[45] Date of Patent: Nov. 26, 1991

[54] STABILIZED POLYISOCYANATES

[75] Inventors: Josef Pedain, Cologne; Lothar Kahl, Bergisch Gladbach; Karl-Arnold Weber, Betzweiler, all of Fed. Rep. of Germany

[73] Assignee: Bayer Aktiengesellschaft, Leverkusen, Fed. Rep. of Germany

[21] Appl. No.: 555,872

[22] Filed: Jul. 20, 1990

Related U.S. Application Data

[63] Continuation-in-part of Ser. No. 348,979, May 9, 1989, abandoned.

[30] Foreign Application Priority Data

May 11, 1988 [DE] Fed. Rep. of Germany ....... 3816118

[51] Int. Cl.$^5$ .................. C07C 249/00; C07D 251/00
[52] U.S. Cl. ..................................... 560/331; 544/221
[58] Field of Search ......................... 560/331; 544/221

[56] References Cited

U.S. PATENT DOCUMENTS

| | | |
|---|---|---|
| 3,953,387 | 4/1976 | Wolgemuth et al. . |
| 4,077,989 | 3/1978 | Schafer et al. . |
| 4,578,472 | 3/1986 | Yoshimura et al. . |
| 4,582,888 | 4/1986 | Kase et al. . |
| 4,720,535 | 1/1988 | Schleier et al. . |

FOREIGN PATENT DOCUMENTS 0254177 1/1988 European Pat. Off. .

OTHER PUBLICATIONS

G. W. Becker/D. Braun, Kunststoff Handbuch, vol. 7, 1983, "Polyurethanes" G. Oertel, Carl Hanser Verlag, pp. 510–546 (english trans.).
H. Kittle, Lehrbuch der Lacke und Beschichtungen, Verlag, W. A. Colomb, Berlin, 1973, vol. I, part II.
K. C. Frisch, P. Korodomenos, American Chemical Society Symposium, 285, "Applied Polymer Science", pp. 985–1029, 2nd ed., Washington, 1985.

Primary Examiner—Alan Siegel
Attorney, Agent, or Firm—Joseph C. Gil; Thomas W. Roy

[57] ABSTRACT

The present invention is directed to polyisocyanates containing a stabilizing amount of a carboxylic acid corresponding to the formula

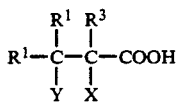

wherein
$R^1$, $R^2$ and $R^3$ represent hydrogen or $C_1$–$C_5$-alkyl and
X and Y represent hydrogen, chlorine or methyl, with the proviso that when X=Cl, Y=H or $CH_3$ and when Y=Cl, X=H or $CH_3$.

The present invention is also directed to the use of the stabilized polyisocyanates as binders for coating compositions, sealing compounds and adhesives.

6 Claims, No Drawings

STABILIZED POLYISOCYANATES

CROSS REFERENCE TO RELATED APPLICATION

This application is a continuation-in-part of U.S. application Ser. No. 07/348,979, filed May 9, 1989 now abandoned.

BACKGROUND OF THE INVENTION

1. Field of the Invention

The present invention is directed to polyisocyanates stabilized with certain chlorine-substituted carboxylic acids.

2. Description of the Prior Art

The polyisocyanates used for lacquers and coatings are generally reaction products of diisocyanates. The diisocyanates are modified by urethanization, urea formation, allophanatization, biuretization, trimerization, dimerization and similar reactions. The polyisocyanates thus modified often contain very little, if any, unreacted starting diisocyanate. However, they contain highly reactive NCO groups which are to be used for subsequent applications. These NCO groups have to remain stable and unreacted for prolonged periods during processing.

It has already been proposed to stabilize modified polyisocyanates by the addition of certain compounds that are generally acidic in character. A stabilizer has to perform several functions, i.e., it has to bind and deactivate reaction accelerators and catalysts which may have been used in previous reactions or which may be unintentionally contained in reactants such as polyethers or polyesters; it has to prevent the polyisocyanate from being adversely affected by light or similar outside influences and must not itself produce any changes such as discoloration; it has to ensure that the polyisocyanate remains stable and retains its high reactivity; it has to ensure that the reactivity of the polyisocyanate to reagents such as polyalcohols or optionally blocked polyamines is reproducible; and it must also be a catalyst for these reactions.

It follows from this that in the context of the present invention, "stabilizers" are not the polyurethane foam stabilizers which have long played an important part in isocyanate chemistry and are not surface-active agents, for example based on polysiloxanes.

The synthesis of polyisocyanates which are suitable for coating purposes or which are useful for adhesives and sealing compounds has been described in numerous publications, of which the following are cited as examples:

1. G. W. Becker and D. Braun, Kunststoff Handbuch, Vol. 7 "Polyurethane", edited by G. Oertel, Carl-Hanser-Verlag, Munchen, Wien 1983, pages 540–610.
2. J. H. Saunders and K. C. Frisch, "High Polymers", Interscience Publishers, New York 1962, Vol. XVI
3. H. Kittel, Lehrbuch der Lacke und Beschichtungen, Verlag W. A. Colomb Berlin 1973, Vol. I, Part 2
4. K. C. Frisch, P. Kordomenos, American Chemical Society Symposium, 285, "Applied Polymer Science", page 985, 2nd Edition, Washington 1985.

The modification of polyisocyanates used for coating compositions, sealing compounds and adhesives by the addition of certain acids or acidic substances for the purpose of stabilization and/or control of reactivity with respect to certain reactants, such as polyols or optionally blocked polyamines, has been described in several publications. According to EP-A 155,559, for example, basic catalysts present in isocyanurate polyisocyanates are neutralized by acids such as phosphoric acid, dodecylbenzene sulfonic acid, monochloroacetic acid, monofluoroacetic acid or benzoyl chloride, and the polyisocyanates are thus stabilized. According to EP-A 239,834 and EP-A 254,177, compounds such as formic acid, acetic acid, mono-, di- and trichloroacetic acid, oxalic acid, malonic acid, maleic acid, fumaric acid, benzoic acid, mono-, di- and trichlorobenzoic acid, salicylic acid, toluenesulfonic acid, xylenesulfonic acid, etc., are added to polyisocyanates containing urethane groups. The effect of this addition is that the polyisocyanates mentioned show constant reactivity to reactants such as polyaldimines, and react with these reactants in the presence of moisture. The additives also influence the hydrolysis rate of the polyaldimines.

The known additives mentioned above only satisfy some of the above-stated requirements for a stabilizer. Some of them even have adverse effects and inter alia discolor the polyisocyanate or impair the stability of the coating compositions, sealing compounds and adhesives in the presence of hydrolytic influences. Their effect can diminish during storage so that the properties of the polyisocyanates to be stabilized can change. Because of this, it has also been proposed to additionally use other stabilizers such as phenothiazines, sterically hindered phenols, etc. (Cf. EP-A 239,834).

Accordingly, an object of the present invention is to provide modified polyisocyanates showing improved stability in storage. This object has surprisingly been achieved by the effectiveness of special carboxylic acids as stabilizers in accordance with the present invention.

SUMMARY OF THE INVENTION

The present invention is directed to polyisocyanates containing a stabilizing amount of a carboxylic acid corresponding to the formula

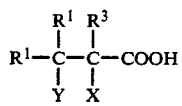

wherein
$R^1$, $R^2$ and $R^3$ represent hydrogen or $C_1$–$C_5$-alkyl and
X and Y represent hydrogen, chlorine or methyl, with the proviso that when X=Cl, Y=H or $CH_3$ and when Y=Cl, X=H or $CH_3$.

The present invention is also directed to the use of the stabilized polyisocyanates as binders for coating compositions, sealing compounds and adhesives.

DETAILED DESCRIPTION OF THE INVENTION

The chlorocarboxylic acids to be used in accordance with the invention are known and include 3-chloro-2,2-dimethyl propanoic acid, 2-chlorobutanoic acid and 2- and 3-chloropropanoic acid. 2-chloropropanoic acid is particularly preferred.

These acids are added to the modified polyisocyanate or homogeneously incorporated therein in a quantity of about 0.0001 to 1% by weight, preferably about 0.001 to 0.1% by weight, based on the weight of the modified polyisocyanate. The acids to be used in accordance with the invention may also be added during the production of the modified isocyanate.

Any unmodified, monomeric polyisocyanates, preferably diisocyanates, and also modified polyisocyanates which, in addition to free NCO groups, also contain urethane groups, allophanate groups, urea groups, biuret groups, isocyanurate groups and/or uretdione groups may be stabilized in accordance with the invention. The modified polyisocyanates do not contain carbodiimide or acylated urea groups because the carboxylic acid stabilizers react with carbodiimide groups to form acylated urea groups.

The unmodified, monomeric polyisocyanates include diisocyanates such as 2,4- and 2,6-toluylene diisocyanate, 2,4'- and 4,4'-diphenylmethane diisocyanate, 1,6-hexamethylene diisocyanate, 1-isocyanato-3,3,5-trimethyl-5-isocyanatomethyl cyclohexane, 2,4'- and 4,4'-dicyclohexylmethane diisocyanate and mixtures of these diisocyanates. These diisocyanates may also be used to prepare the modified polyisocyanates. Other diisocyantes and modification products thereof are mentioned, for example, in DE-A 2,637,115, i.e., polyisocyanates or NCO prepolymers which form polyurethane ureas with water and a hardener mixture based on compounds corresponding to the following general formulae $$H_2N-R-NH_2 \quad (A)$$

$$H_2N-R-N=R_1 \quad (B)$$

$$R_1=N-R-N=R_1 \quad (C)$$

wherein

R is a difunctional aliphatic, cycloaliphatic or araliphatic radical and $R_1$ is an aliphatic or cycloaliphatic radical of the type formed by removal of the oxygen from a ketone or aldehyde.

The following molar ratios $$\frac{A}{B+C} = 1:20 \text{ to } 1:3$$

$$\frac{B}{C} = 1:2 \text{ to } 2:1 \text{ and}$$

$$\frac{A+B+C}{H_2O} = 1:1.4 \text{ to } 1:20$$

are maintained among the components.

The modified polyisocyanates described in DE-A 2,637,115 (U.S. Pat. No. 4,108,842, herein incorporated by reference), DE-A 3,011,711, EP-A 3569 (U.S. Pat. No. 4,242,410, herein incorporated by reference) are particularly suitable for stabilization. The polyisocyanates described in EP-A 0,254,177 and in EP-A 0,239,834 (U.S. Pat. No. 4,720,535, herein incorporated by reference) which are useful in coating compositions, may also be very effectively stabilized or standardized in their reactivity to polyaldimines. Other modified polyisocyanates, which may be stabilized with advantage in accordance with the invention are described in DE-A 2,641,448 (U.S. Pat. No. 4,124,569, herein incorporated by reference).

The products stabilized in accordance with the invention show remarkable advantages over the prior art, i.e., they show improved stability in storage, in particular the color, viscosity and NCO content of the polyisocyanates remain constant for long periods; and they may be processed more easily and reproducibly with reactants, especially in combination with polyaldimines (for example according to EP-A 254,117) and polyketimines (for example according to DE-A 2,637,115). Coatings having the same properties may be repeatedly produced with the products according to the invention.

The invention is further illustrated but is not intended to be limited by the following examples in which all parts and percentages are by weight unless otherwise specified.

EXAMPLES

Example 1

6000 g (3.53 mole) of a hydroxyl polyester of adipic acid, hexane-1,6-diol and neopentyl glycol (molar ratio of diols 65:35) were dehydrated in vacuo at 120° C., mixed with 1290 g (7.41 moles) toluylene diisocyanate (80% 2,4-, 20% 2,6-isomer) and reacted for 30 minutes at 90° C. 320 g of a mixed trimer based on 2,4-toluylene diisocyanate and 1,6-hexamethylene diisocyanate in a molar ratio of 3:2 (5 mole-%, based on the isocyanate component as a whole) were then added and the reaction mixture was left to react for 30 minutes at 90° C., cooled to 60° C. and diluted with 1900 g ethyl acetate. NCO content of the polyisocyanate obtained: 3.45% by weight of the approx. 80% solution.

Repetition of the test produced an NCO content of 3.62% by weight and an 80% solution.

Example 2

6039 g of the hydroxyl polyester of Example 1 were mixed with 1655 g of 1-isocyanato-3,3,5-trimethyl-5-isocyanatomethyl cyclohexane and the resulting mixture was reacted with stirring for 5 hours at 100° C. to form an NCO prepolymer. 314 g of the mixed trimer described in Example 1 were then mixed in, followed by stirring for a few minutes at 60° C. The product was then dissolved to form an approximately 80% solution in ethyl acetate having an NCO content of 3.28% and a viscosity of 4200 mPa.s.

Example 3

A mixture of 1700 g 3,3,5-trimethyl-5-aminomethyl cyclohexylamine (IPDA), 130 g water and 4170 g methyl ethyl ketone was boiled under reflux for 2 hours. After cooling, the hardener was ready for use. It contained free amino groups and ketimine groups.

Example 4

The procedure was as described in Example 1 with the following difference: after dehydration of the polyester, 200 ppm (based on the mixture excluding solvent) of 2-chloropropionic acid were added and thoroughly mixed in. The procedure was then as described in Example 1, i.e., reaction with toluylene diisocyanate and mixing with the mixed trimer of toluylene diisocyanate and hexamethylene diisocyanate. The 80% solution in ethyl acetate had an NCO content of 3.52% by weight.

Examples 5 to 17

In these examples, a stabilizer according to the invention was compared in its effectiveness with known stabilizers. The stabilizers were added to the polyisocyanate solution of Example 1 (in Example 17, which was based on Example 4, the stabilizer was already present) at about 25° C. in a quantity of 200 ppm (based on solvent-free product) and mixed by stirring until a clear homogeneous liquid was formed.

The changes in NCO content, color and reactivity during storage were investigated. The samples were stored in colorless glass bottles in the absence of moisture at room temperature, i.e., at about 23° C. in daylight and under artificial laboratory lighting, i.e., conditions which are encountered in use. The NCO content and color were investigated using approximately 80% solutions.

Reactivity was measured using the hardener of Example 3 which contained amino groups and ketimine groups. To measure reactivity, the particular polyisocyanate was diluted with a 1:1 mixture of toluene and ethyl acetate to a content of 50% by weight and then rapidly homogeneously mixed by thorough stirring with the hardener of Example 3 which had not been further diluted. A ratio of NCO groups to amino groups (free or ketone-blocked) of 1.08:1 was maintained. The time which the mixture took to reach a viscosity of 60,000 mPa.s at 23° C. was measured. To guarantee satisfactory coating, for example of skiver in accordance with DE-A 2,637,115, experience has shown that this time should be no longer than about 250 to 270 seconds.

vided good results in regard to NCO content and reactivity, although color was slightly affected.

Examples 18 to 28

The procedure was as in Examples 5 to 17, except that the polyisocyanate of Example 2 was investigated. Stabilizers from the prior art and stabilizers according to the invention were again used for stabilization. Quantities of 200 ppm stabilizer were homogeneously incorporated at room temperature (approx. 23° C.) in the 80% solution of the polyisocyanate. As in Examples 5 to 17, NCO content, discoloration and reactivity before and after storage were investigated in colorless glass bottles at about 23° C. Reactivity was measured with respect to the hardener of Example 3. Both solutions were used without further dilution.

The ratio of NCO groups to amino groups (free or ketone-blocked) was 1.1. The time which the mixture took to reach a viscosity of 60,000 mPa.s was measured. This time again should be less than 300 seconds to allow problem-free processing on high-speed coating machines.

TABLE 2

| Example | Stabilizer | NCO content Fresh | (% by weight) After 21 days | Color Fresh | After 21 days | Reactivity (seconds) Fresh | After 21 days |
| --- | --- | --- | --- | --- | --- | --- | --- |
| 18 | — none | 3.3 | 2.9 | colorless | yellow | 397 | 520 |
| 19 | benzoyl chloride | 3.3 | 3.12 | light yellow | yellow-brown | 238 | 743 |
| 20 | formic acid | 3.28 | 2.98 | colorless | light yellow | 273 | 315 |
| 21 | acetic acid | 3.28 | 2.95 | colorless | yellow | 198 | 295 |
| 22 | p-toluenesulfonic acid | 3.28 | 2.95 | colorless | dark yellow | 276 | 350 |
| 23 | dichloroacetic acid | 3.3 | 3.15 | colorless | yellow | 286 | 344 |
| 24 | 3-chloropropionic acid amide | 3.3 | 3.00 | colorless | light yellow | 290 | 410 |
| 25 | perfluorobutanesulfonic acid | 3.3 | 3.18 | pale yellow | yellow-brown | 203 | 246 |
| 26 | monofluoroacetic acid | 3.28 | 2.97 | colorless | dark yellow | 199 | 266 |
| 27 | 2-chloropropionic acid | 3.28 | 3.18 | colorless | colorless | 224 | 238 |
| 28 | 3-chloropropionic acid | 3.28 | 3.10 | colorless | colorless | 208 | 240 |

TABLE 1

| Example | Stabilizer | NCO Content Fresh | (% by weight) After 4 Weeks | Color Fresh | After 4 weeks | Reactivity (seconds) Fresh | After 4 weeks | After 8 Weeks |
| --- | --- | --- | --- | --- | --- | --- | --- | --- |
| 5 | — none | 3.45 | 3.05 | colorless | yellow | 270 | 460 | 600 |
| 6 | benzoyl chloride | 3.45 | 3.40 | light yellow | brown-yellow | 161 | 325 | 405 |
| 7 | isophthalyl chloride | 3.45 | 3.30 | colorless | dark yellow | 163 | 271 | 330 |
| 8 | p-toluenesulfonic acid | 3.45 | 3.32 | yellow-brown/hazy | red-brown | 154 | 450 | 503 |
| 9 | perfluorobutanesulfonic acid | 3.62 | 3.6 | colorless | bright yellow | 150 | 203 | 280 |
| 10 | methanesulfonic acid | 3.62 | 3.45 | colorless | yellow | 303 | 297 | 370 |
| 11 | acetic acid | 3.45 | 3.23 | colorless | bright yellow | 249 | 210 | 230 |
| 12 | dichloroacetic acid | 3.62 | 3.45 | colorless | dark yellow | 180 | 297 | 340 |
| 13 | monofluoroacetic acid | 3.62 | 3.30 | pale yellow | dark yellow | 240 | 298 | 320 |
| 14 | formic acid | 3.45 | 3.25 | pale yellow | bright yellow | 287 | 309 | 450 |
| 15 | 2-chloropropionic acid | 3.45 | 3.40 | colorless | colorless | 230 | 256 | 270 |
| 16 | 2-chloropropionic acid | 3.62 | 3.55 | colorless | light yellow | 205 | 238 | 261 |
| 17 | 2-chloropropionic acid | 3.45 | 3.33 | pale yellow | pale yellow | 273 | 268 | 270 |

Result

All the stabilizers produced a constant NCO content. Comparison Examples 5 to 14 show that known stabilizers were not able to provide the required stabilization against discoloration. In addition, most of the conventional stabilizers were unsuitable for stabilizing reactivity. Examples 15, 16 and 17 according to the invention showed the best results in regard to the stabilization of NCO content, color and reactivity. Addition of the stabilizer during the reaction (Example 17) also pro-

Result

Comparison of all the stabilizers tested demonstrated that Examples 27 and 28 according to the invention produced the best stabilization results, even in the case of the aliphatic polyisocyanate, in regard to all of the properties investigated.

Application Example 100 g of the prepolymer of Example 1, 45.6 g of the hardener of Example 3, 6.8 g of a colored pigment and 0.1 g 2-chloropropionic acid were mixed in a two-component spray gun of the EMU 10 type made by Maschinenfabrik Hennecke (Federal Republic of Germany) and the resulting mixture was sprayed onto a female mold. (The gun was mechanically moved back and forth while the female mold, arranged perpendicularly of the direction of movement of the gun, advanced uniformly beneath the gun).

After various time intervals from the time of application of the mixture, nonwovens or skiver were laid on by hand and uniformly pressed on mechanically by rollers.

The coated parts then passed through a drying tunnel heated to around 80° C. After 4 minutes, the parts were removed from the female mold. The coatings had a leather-like grain which remained fully intact on stacking, were completely tack-free and could be processed at high speed on shoemaking machines. The coated parts were resistant to chemicals and water. In a flex test, they withstood flexing more than 2000 times at −25° C. without damage.

The properties demonstrate that the polyurethane urea formed had fully reacted under the effect of the stabilizer according to the invention.

When the same test was repeated with an isocyanate prepolymer of Example 1 without the addition of 2-chloropropionic acid, the coatings obtained could only be removed after 8 minutes and could only be stacked and processed after storage for 24 hours.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A modified polyisocyanate which is free from carbodiimide or acylated urea groups and contains free isocyanate groups and a member selected from the group consisting of urethane groups, allophanate groups, urea groups biuret groups, isocyanurate groups, uretdione groups and mixtures thereof and a stabilizing amount of a carboxylic acid corresponding to the formula

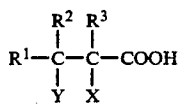

wherein
$R^1$, $R^2$ and $R^3$ represent hydrogen or $C_1$–$C_5$-alkyl and
X and Y represent hydrogen, chlorine or methyl, with the proviso that when Y=H or $CH_3$, X=Cl, and when X=H or $CH_3$, Y=Cl.

2. The polyisocyanate of claim 1 wherein the carboxylic acid comprises 2-chloropropionic acid.

3. The polyisocyanate of claim 1 wherein the carboxylic acid comprises 3-chloropropionic acid.

4. The polyisocyanate of claim 1 wherein said carboxylic acid is present in an amount of about 0.001 to 1.0% by weight, based on the weight of the polyisocyanate.

5. The polyisocyanate of claim 2 wherein said carboxylic acid is present in an amount of about 0.001 to 1.0% by weight, based on the weight of the polyisocyanate.

6. The polyisocyanate of claim 3 wherein said carboxylic acid is present in an amount of about 0.001 to 1.0% by weight, based on the weight of the polyisocyanate.